(12) United States Patent
Savall et al.

(10) Patent No.: US 11,786,315 B2
(45) Date of Patent: Oct. 17, 2023

(54) SURGICAL ROBOTIC SYSTEM HAVING GRIP-DEPENDENT CONTROL

(71) Applicant: Verb Surgical Inc., Santa Clara, CA (US)

(72) Inventors: Joan Savall, Palo Alto, CA (US); Denise Ann Miller, Scotts Valley, CA (US); Karan Handa, San Mateo, CA (US)

(73) Assignee: Verb Surgical Inc., Santa Clara, CA (US)

( * ) Notice: Subject to any disclaimer, the term of this patent is extended or adjusted under 35 U.S.C. 154(b) by 414 days.

(21) Appl. No.: 17/026,085

(22) Filed: Sep. 18, 2020

(65) Prior Publication Data
US 2022/0087748 A1 Mar. 24, 2022

(51) Int. Cl.
*G09G 5/00* (2006.01)
*A61B 34/20* (2016.01)
*A61B 34/00* (2016.01)
*A61B 34/37* (2016.01)
*A61B 34/30* (2016.01)

(52) U.S. Cl.
CPC .............. *A61B 34/20* (2016.02); *A61B 34/25* (2016.02); *A61B 34/37* (2016.02); *A61B 34/74* (2016.02); *A61B 34/76* (2016.02); *A61B 2034/2046* (2016.02); *A61B 2034/301* (2016.02); *A61B 2562/0257* (2013.01)

(58) Field of Classification Search
CPC .. A61B 2017/00207; A61B 2034/2046; A61B 2034/2051; A61B 2034/301; A61B 2562/0257; A61B 34/20; A61B 34/25; A61B 34/37; A61B 34/74; A61B 34/76
See application file for complete search history.

(56) References Cited

U.S. PATENT DOCUMENTS

2014/0148820 A1\* 5/2014 Ogawa .................... A61B 34/77
606/130
2020/0276497 A1\* 9/2020 Nietfeld .................. G06F 3/014

\* cited by examiner

*Primary Examiner* — Insa Sadio
(74) *Attorney, Agent, or Firm* — Aikin & Gallant, LLP (57) ABSTRACT

Surgical robotic systems, and methods of controlling such systems based on a user's grip on a user interface device, are described. During a surgical procedure, a surgical robotic system generates control commands to actuate a component of the surgical robotic system. The component can be a surgical tool that is actuated to move based on tracking data from the user interface device. The component can be the user interface device, which is actuated to render haptic feedback to the user's hand based on load data from a surgical robotic arm holding the surgical tool. In either case, the actuation is based on a center of rotation of the user interface device that corresponds to the user's grip on the user interface device. Other embodiments are described and claimed.

20 Claims, 7 Drawing Sheets

SURGICAL ROBOTIC SYSTEM HAVING GRIP-DEPENDENT CONTROL

BACKGROUND

Field

Embodiments related to robotic systems are disclosed. More particularly, embodiments related to surgical robotic systems having user interface devices are disclosed.

Background Information

Endoscopic surgery involves looking into a patient's body and performing surgery inside the body using endoscopes and other surgical tools. For example, laparoscopic surgery can use a laparoscope to access and view an abdominal cavity. Endoscopic surgery can be performed using manual tools and/or a surgical robotic system having robotically-assisted tools.

A surgical robotic system may be remotely operated by a surgeon to command robotically-assisted tools or a camera located at an operating table. The surgeon may use a user console located in the operating room (or in a different city) to command a robot to manipulate the surgical tool and the camera. For example, the surgeon may hold in her hand a user input device such as a joystick or a computer mouse that she manipulates to generate control commands that cause motion of the surgical robotic system components, e.g., the surgical tool or the camera. The robot can use the surgical tools to perform surgery, with the visualization aid provided by the camera.

Accurate control of robotically-assisted tools is important to reaching a favorable clinical outcome with robotic surgery. Such control typically requires that an input movement of the user input device be accurately translated to a corresponding movement of a robotically assisted tool.

SUMMARY

User input devices used to generate control commands to cause motion of surgical robotic system components may be ungrounded. For example, a user input device can be held by the surgeon and freely manipulated in space without being mechanically linked to another structure in the operating room. In such case, a center of rotation of the user input device can be mapped to a center of rotation of the surgical tool. Accordingly, when the surgeon moves, e.g., tilts or rotates, the user input device, a corresponding movement of the surgical tool can occur. The center of rotation can be fixed, e.g., to coincide with a tracking sensor in the user interface device used to track movement of the user interface device. The fixed center of rotation, however, may not match the expectation of the surgeon. For example, when the surgeon grips the user interface device in front of or behind the fixed center of rotation, the surgeon may expect the center of rotation to be between her fingers at a location that is offset from the fixed center of rotation. As a result, the surgeon may move the user input device expecting a corresponding movement of the surgical tool, but the surgical tool may move in a different manner that does not accurately emulate the expected movement of the surgeon. Accordingly, a surgical robotic system that determines a virtual center of rotation matching the expectation of the user, and that uses the virtual center of rotation to control the surgical tool, can contribute to accurate control of the surgical robotic system and successful robotic surgery.

A surgical robotic system and a method of controlling such systems based on a user's grip on a user interface device, are provided. In an embodiment, the method includes determining a grip configuration of a user's hand on the user interface device. The user interface device can include proximity sensors, such as time-of-flight sensors or capacitive sensors, which detect the positions of the fingers of the user's hand. The grip configuration can be defined based on the finger positions. For example, when the finger positions are near a distal end of the user interface device, the grip configuration can be an anterior grip, and when the finger positions are near a proximal end of the user interface device, the grip configuration can be a posterior grip.

The method includes determining, based on the grip configuration, a center of rotation of the user interface device. The user interface device can include a tracking sensor to detect movement of the user interface device. More particularly, the movement may be detected about a sensor center of rotation, e.g., tracking data can describe movement of the user interface device relative to the sensor center of rotation. By contrast, the virtual center of rotation determined based on the grip configuration may be offset from sensor center of rotation. The virtual center of rotation can be set to a predetermined location based on whether the grip is anterior to or posterior to the sensor center of rotation. The virtual center of rotation can be set based on geometrical analysis of the positions of the user's fingers. In any case, the virtual center of rotation can be an estimation of the center of rotation expected by the user.

The surgical robotic system can control movement of a component based on the determined virtual center of rotation of the user interface device. More particularly, the system can generate control commands to actuate the component based on the virtual center of rotation. In an embodiment, the component is a surgical tool, and the control commands actuate the surgical tool based on the virtual center of rotation and the tracking data to move the surgical tool in six degrees of freedom. In an embodiment, the component is the user interface device, and the control commands actuate the user interface device based on the virtual center of rotation and load data corresponding to a force applied to the surgical tool to render haptic feedback to the user's hand emulating the force. In any case, actuation of the component based on the virtual center of rotation expected by the user can provide accurate control of the component in a manner that matches the user's expectation.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Embodiments describe methods of controlling robotic systems based on a user's grip on a user interface device (UID). The UID can control spatial motion of a surgical tool of a surgical robotic system during a robotic surgery. The UID may, however, be used in other robotic systems, such as for manufacturing or military applications, to name only a few possible applications.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction, e.g., along a longitudinal axis of a UID in a first direction. Similarly, "proximal" may indicate a second direction along the longitudinal axis opposite to the first direction. Such terms are provided to establish relative frames of reference, however, and are not intended to limit the use or orientation of a surgical robotic system component to a specific configuration described in the various embodiments below.

In an aspect, a surgical robotic system performs a method of controlling actuation of a system component based on a manner in which a user grips a UID of the system. The grip configuration can be determined based on detection of the user's finger location on the UID. For example, readings from proximity sensors, such as a time-of-flight (TOF) sensors, can be used to estimate the user's finger location on the UID. A control system of the surgical robotic system can use the determined grip configuration to set a center of rotation of the UID. The center of rotation of the UID can correspond to a center of rotation of a surgical tool being controlled by the control system. Accordingly, movement of the UID about the UID center of rotation can be accurately translated to movement of the surgical tool about the tool center of rotation. The center of rotation of the UID can be adjusted in real time to maintain accurate control of the surgical tool throughout the surgical procedure, even as the user changes her grip on the UID.

Figure 1:
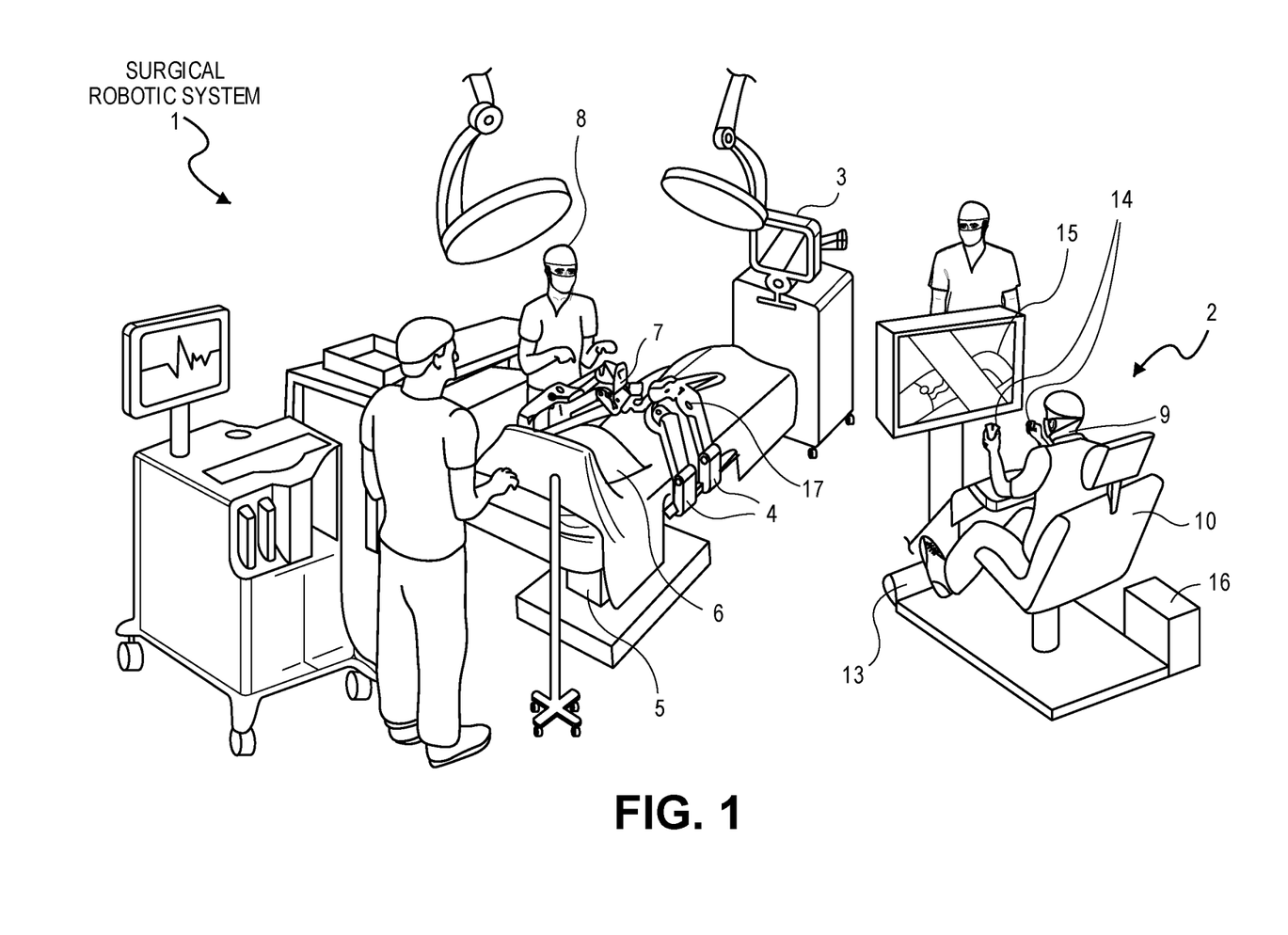
FIG. 1 is a pictorial view of an example surgical robotic system in an operating arena, in accordance with an embodiment.

Referring to FIG. 1, this is a pictorial view of an example surgical robotic system 1 in an operating arena. The system 1 includes a user console 2, a control tower 3, and one or more surgical robotic arms 4 at a surgical robotic platform 5, e.g., a table, a bed, etc. The arms 4 may be mounted to a table or bed on which the patient rests as shown in the example of FIG. 1, or they may be mounted to a cart separate from the table or bed. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In one aspect, the surgical tool 7 is a grasper that can grasp tissue of the patient. The surgical tool 7 may be configured to be controlled manually by a bedside operator 8, robotically via actuated movement of the surgical robotic arm 4 to which it is attached, or both. The robotic arms 4 are shown as being table-mounted but in other configurations the arms 4 may be mounted to a cart, the ceiling or a sidewall, or to another suitable structural support.

A remote operator 9, such as a surgeon or other human operator, may use the user console 2 to remotely manipulate the arms 4 and their attached surgical tools 7, e.g., referred to here as teleoperation. The user console 2 may be located in the same operating room as the rest of the system 1 as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices (UIDs) 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 that are mounted on the distal ends of the arms 4.

In some variations, the bedside operator 8 may operate the system 1 in an "over the bed" mode in which the beside operator 8 (user) is at a side of the patient 6 and is simultaneously manipulating a robotically-driven tool (an end effector that is attached to the arm 4) with a handheld UID 14 held in one hand, and a manual laparoscopic tool in another hand. For example, the bedside operator's left hand may be manipulating the handheld UID to control a robotically-driven tool, while the bedside operator's right hand may be manipulating a manual laparoscopic tool. In this particular variation of the system 1, the bedside operator 8 can perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, which opens or closes jaws of the grasper at a distal end of surgical tool 7 to grip tissue within patient 6.

In some aspects, the communication between the platform 5 and the user console 2 may be through a control tower 3, which may translate user commands that are received from the user console 2 (and more particularly from the console computer system 16) into robotic control commands that transmitted to the arms 4 on the robotic platform 5. The control tower 3 may also transmit status and feedback from the platform 5 back to the user console 2. The communication connections between the robotic platform 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output (video feed) may also be encrypted to ensure privacy and all or portions of the video output may be saved to a server or electronic healthcare record system.

It will be appreciated that the operating room scene in FIG. 1 is illustrative and may not accurately represent certain medical practices.

Figure 2:
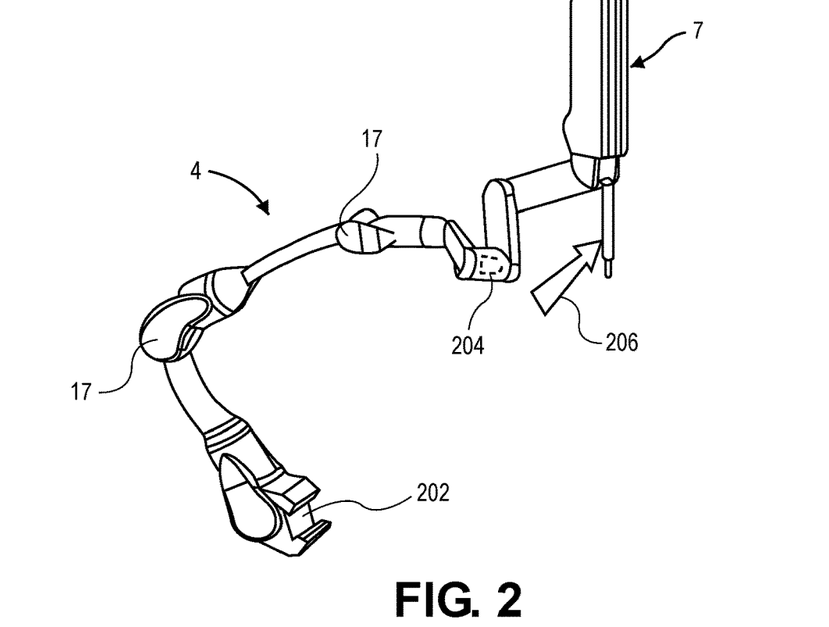
FIG. 2 is a pictorial view of a surgical tool of a surgical robotic system, in accordance with an embodiment.

Referring to FIG. 2, a pictorial view of a surgical tool of a surgical robotic system is shown in accordance with an embodiment. The surgical robotic system 1 includes at least one surgical robotic arm 4. A surgical robotic arm 4 may be coupled to the surgical robotic platform 5 at a mounting location 202, and the surgical tool 7 may be mounted on the surgical robotic arm 4, e.g., at the distal end of the arm. The surgical tool 7 can include a tool driver and a cannula coupled to an end of the tool driver. The cannula can receive and guide a surgical instrument, e.g., a grasper, a camera, etc. Furthermore, the robotic arm 4 may include several links that can be actuated to position and orient the surgical tool 7 in a particular manner. More particularly, the links can be actuated to cause movement of the surgical tool 7 that emulates movement of the UID 14.

Figure 3:
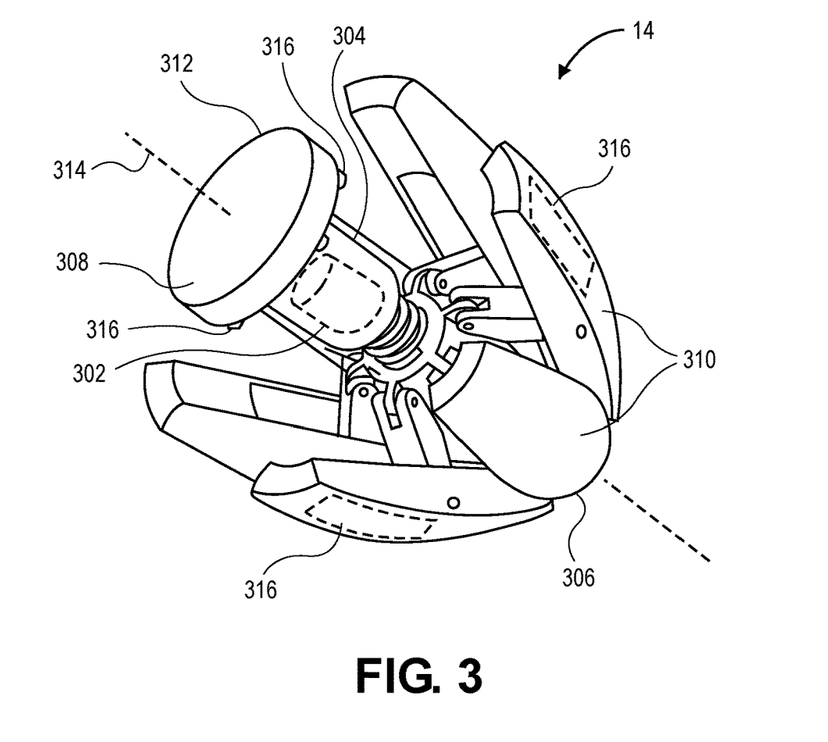
FIG. 3 is a pictorial view of a user interface device of a surgical robotic system, in accordance with an embodiment.

Referring to FIG. 3, a pictorial view of a UID of a surgical robotic system is shown in accordance with an embodiment. As described above, a user, e.g., the remote operator 9, can hold and move the UID 14 to control spatial motion of a corresponding surgical tool 7 of the surgical robotic system 1. The UID 14 can be an ungrounded UID. Accordingly, the UID 14 can have no connection to a supporting structure other than a user's hand, and is capable of being supported and moved freely in space by the user's hand. It will be appreciated, however, that grounded systems having UIDs connected to a supporting structure, e.g., to a support linkage, may also benefit from the methods of grip-dependent control described below.

The UID 14 can include a tracking sensor 302. The tracking sensor 302 may be a six-degree-of-freedom electromagnetic tracker that is used to generate a spatial state signal, e.g., an input pose signal, in response to movement of a device body 304. More particularly, the tracking sensor 302 may be any sensor configured to track movement of the UID 14 in six degrees of freedom. The spatial state signal can be used by one or more processors to generate control signals to control proportional motion of the arm actuator 17 and/or the surgical tool 7 of the surgical robotic system 1. Accordingly, the UID 14 can be used to control highly dexterous, precise movement of the robotic actuator 17 and/or the robotic surgical tool 7. Furthermore, in addition to detecting an orientation of the UID 14, tracking data from the tracking sensor 202 may be used to determine a location, speed, or acceleration of the UID 14.

The UID 14 can include a proximal end 306 and a distal end 308, and several grip components 310 can extend distally from the proximal end 306 toward the distal end 308. The grip components 310 can be gripped by a user and manipulated to generate spatial state signals. For example, the user can rotate, tilt, or translate the UID 14 in free space to cause the control system to generate control commands to cause a corresponding end effector of the surgical tool 7 to move similarly. Similarly, the user can press on the grip components 310 to generate a grip signal for controlling jaws of the corresponding end effector.

Figure 4:
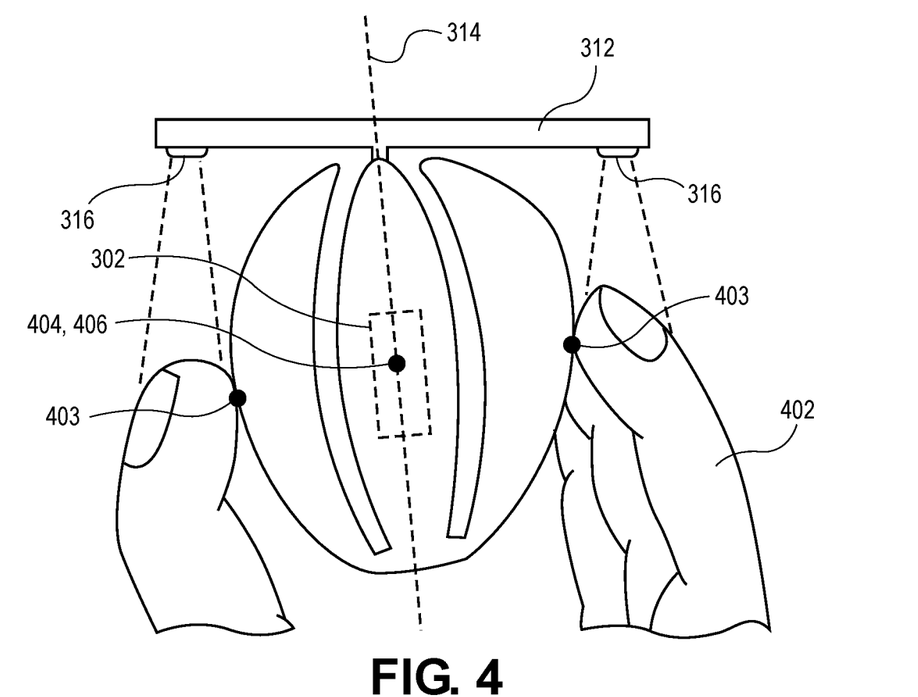
FIG. 4 is a pictorial view of a user interface device being held with a first grip configuration, in accordance with an embodiment.
Figure 5:
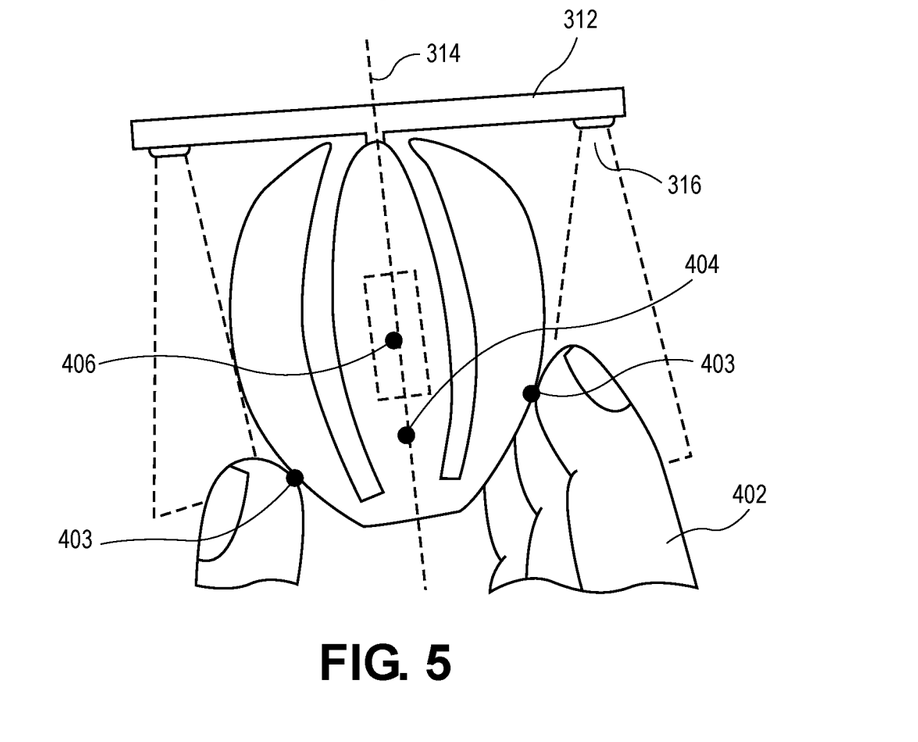
FIG. 5 is a pictorial view of a user interface device being held with a second grip configuration, in accordance with an embodiment.

The UID 14 may also include a device head 312. The device head 312 may be located at the distal end 308 of the UID 14. In an embodiment, the device head 312 has a surface extending transverse to a central axis 314 of the UID 14. The transverse surface may be distal to the grip components 310, and thus, may be axially aligned with the user's hand when the user is gripping the grip component 310 (FIGS. 4-5).

In an embodiment, the UID 14 includes one or more proximity sensors 316. For example, several proximity sensors 316 can be mounted on the device body 304, the device head 312, or another portion of the UID 14, and directed toward the user's hand when the user is gripping the UID 14. The proximity sensors 316 may be mounted on the transverse surface of the device head 312 and the sensing path of the sensors can be directed proximally in a direction of the central axis 314 of the UID 14 to detect the fingers of the user when the user is gripping the grip components 310. For example, the UID 14 can include three or more, e.g., six, proximity sensors 316 evenly distributed around the central axis 314 of the device body 304 on the device head 312. The proximity sensors 316 may be distributed such that the sensor group is able to detect the presence and/or position of the fingers at any location around the device body 304. More particularly, the proximity sensors 316 can detect a target within an annular target zone extending around the device body 304. Accordingly, in addition to receiving tracking data from the tracking sensor 302 indicative of a location or movement of the UID 14, the surgical robotic system 1 can receive proximity data from the proximity sensors 316 indicative of whether the UID 14 is being held by the user, or indicative of whether an object is adjacent to or near the proximity sensors 316.

The proximity data from the proximity sensors 316 may be used to provide drop detection for the surgical robotic system 1. Proximity data from the proximity sensors 316 can indicate the presence of the user's hand when the user is holding the UID 14, and by contrast, can indicate the absence of the user's hand when the user is not holding the UID 14. Accordingly, the proximity data can indicate a change from the presence of the user's hand to the absence of the user's hand when the user drops the UID 14. In an embodiment, the surgical robotic system 1 can halt motion of the surgical tool 7 in response to detecting the drop condition based on the proximity data. Such drop detection and control of the surgical tool 7 can provide a safety feature to avoid unintended movements of the surgical tool 7 that could harm the patient 102.

In an embodiment, the proximity sensors 316 include sensors to detect touch on an outer surface of the grip components 310. For example, each grip component 310 can include a proximity sensor 316 to detect a location that the user's finger is placed on the outer surface. The proximity sensors 316 of the grip components 310 may be used instead of, or in combination with, the proximity sensors 316 mounted on the device head 312. Accordingly, the UID 14 can have proximity sensors 316 distributed around the central axis 314 of the device body 304 to detect the presence of the user's fingers at any location on the outer surface of the device body 304.

The proximity sensors 316 can include sensors that detect the presence of nearby objects without physically contacting the objects. A variety of proximity sensor types exist that may be incorporated into the UID 14 for such purpose. For example, the proximity sensors 316 can be capacitive proximity sensors, photoelectric sensors, or other types of proximity sensors. In an embodiment, the proximity sensors 316 include time-of-flight (TOF) sensors. The TOF sensors may be mounted on the device head 312 and can be used for range imaging. For example, the TOF sensors can emit a beam of electromagnetic radiation, e.g., an infrared laser beam emitted by an infrared laser source of the sensor, and measure a return signal reflected by a nearby object to determine a presence of or a distance to the nearby object. Accordingly, the proximity sensors 316 can be TOF sensors to generate proximity data indicative of whether an object is adjacent to or near the proximity sensors 316. More particularly, the proximity data can be TOF data output by TOF sensors indicative of a distance from the TOF sensors to the fingers of the user. A position of the fingers on the UID 14 can be determined based on the TOF data.

The proximity sensors 316 may include capacitive sensors mounted on or within the grip components 310. For example, the capacitive sensors may overlay the outer surface of the device body 304. The capacitive sensors may sense touch, e.g., a presence of the user's fingers on the outer surface. Accordingly, the proximity sensors 316 can be capacitive sensors to generate proximity data indicative of whether and how the user is holding the UID 14. More particularly, the proximity data can be capacitive sensor data output by capacitive sensors indicative of a user's grip on the UID 14. A position of the fingers on the UID 14 can be determined based on the capacitive sensor data.

Referring to FIG. 4, a pictorial view of a UID being held with a first grip configuration is shown in accordance with an embodiment. A grip configuration of a user's hand 402 on the UID 14 can be detected by the proximity sensors 316. For example, TOF sensors mounted on the device head 312 can measure a distance from the sensor to the fingers of the user. Based on the distance, a position of each of the fingers on the outer surface of the device body 304 may be determined. These positions, e.g., contact points 403 between the fingertips of the user and the outer surface, can define the grip configuration. For example, in the grip configuration shown in FIG. 4, the user's fingers can grip the device body 304 radially around the tracking sensor 302. Although the grip configuration is shown as being detected by the TOF sensors on the device head 312, it will be appreciated that the grip configuration can be detected by capacitive sensors mounted on the outer surface of the UID 14.

The UID 14 can have a center of rotation 404. By default, the center of rotation 404 can be defined as a center of the tracking sensor 302 that is used to determine the six-degree-of-freedom position and orientation of the UID 14. For example, the tracking sensor 302 can have a sensor center of rotation 406 about which rotation of the tracking sensor 302 is tracked. The sensor center of rotation 406 may by default coincide with a center of mass of the device body 304. For example, the tracking sensor 302 may be integrated in the UID 14 such that the sensor center of rotation 406 is located at the center of mass of the UID 14. The default center of rotation 404 may be so-positioned because it may be assumed that the user will grip the UID 14 in the first configuration with the user's fingers near the middle of the device body 304 and radially around, e.g., at a same axial location, as the tracking sensor 302. The user may, however, grip the UID 14 at an axial location offset from the sensor center (FIG. 5). For example, the user may hold the controller in multiple grip configurations as the user changes the grip when manipulating the handheld UID 14 during surgery. Each time the grip is changed, the user may expect the center of rotation 404 to change because the intuitive user expectation is that the center of rotation 404 will be centered within the contact points 403 along the central axis 314. The center of rotation 404 may be adjusted to match the user expectation by moving the virtual center of rotation 404 to a location offset from the sensor center of rotation 406.

Referring to FIG. 5, a pictorial view of a UID being held with a second grip configuration is shown in accordance with an embodiment. In the second configuration, the user's fingers may be moved backward, or proximally, in the direction of the central axis 314. The contact points 403 may therefore be behind (posterior to) the sensor center of rotation 406 as the user changes the grip position. In an embodiment, as the grip configuration changes, the expected center of rotation 404 changes. More particularly, the user may expect the center of rotation 404 to be radially inward from her fingertips regardless of where the user grips the device body 304. Accordingly, when the user has the second grip configuration, the user may expect the center of rotation 404 to be posterior to the sensor center of rotation 406 of the tracking sensor 302. Similarly, when the user has a third grip configuration (not shown) with her fingertips in front of (anterior to) the sensor center of rotation 406, the user may expect the center of rotation 404 to be anterior to the sensor center of rotation 406. In any case, the user may expect the center of rotation 404 to be at a location along the central axis 314 that does not coincide with the sensor center of rotation 406.

Figure 6:
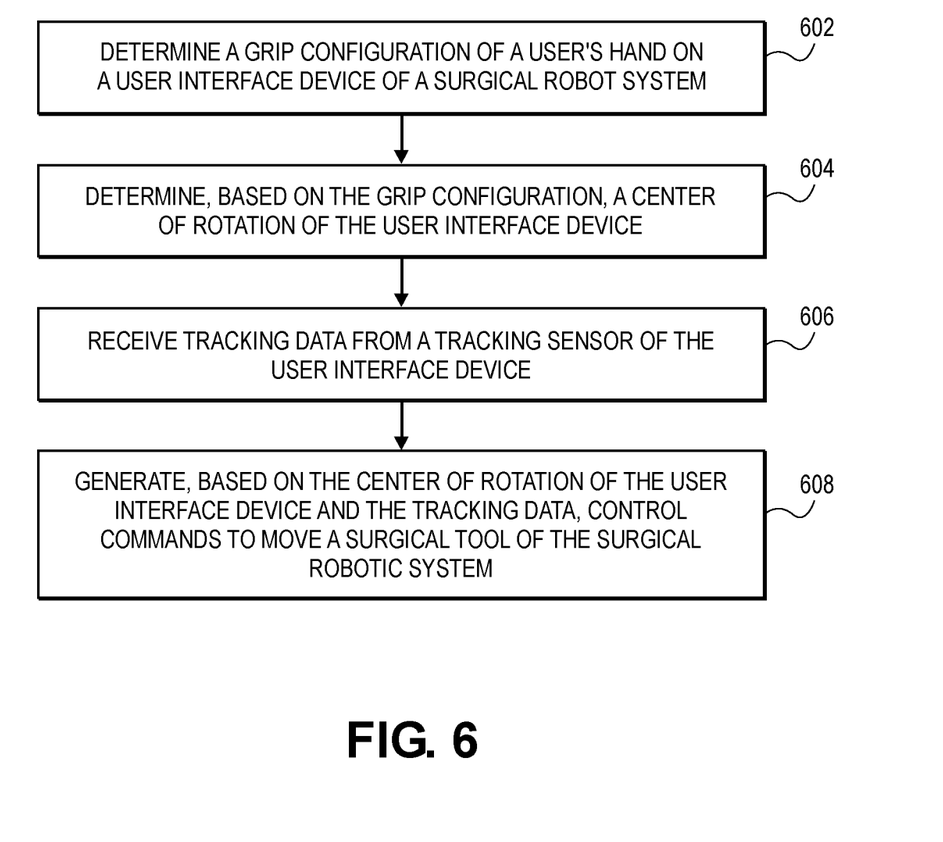
FIG. 6 is a flowchart of a method of actuating a surgical tool of a surgical robotic system based on a center of rotation of a user interface device, in accordance with an embodiment.

Methods of controlling a component of the surgical robotic system 1 based on the user's grip on the UID 14 are described below. The method can include grip-dependent active or passive control of the component. For example, FIG. 6 includes a flowchart of a method of actuating the surgical tool 7 of the surgical robotic system 1 based on the center of rotation 404 of the UID 14 (active control). FIG. 9 includes a flowchart of a method of actuating the UID 14 based on the center of rotation 404 (passive control). FIG. 6 is referred to first in combination with FIGS. 7-8, which illustrate certain operations of the methods. It will be appreciated, however, that the methods are specific embodiments of a generalized method of grip-dependent control of a component of the surgical robotic system 1, and certain operations can apply to any of the methods described herein.

Referring to FIG. 6, for passive controllers, modifying the center of rotation 404 to coincide with an expectation of the user can provide optimal mapping between an input by the user, e.g., a movement of the UID 14, and output orientations, e.g., movement of the surgical tool 7. To ensure optimal control using the UID 14, a virtual center of rotation 404 may be determined and used by the control system to control movement of the surgical tool 7 based on the UID 14 movements. The virtual center of rotation 404 can be a non-default center of rotation 404 that, rather than being based on the fixed sensor center of rotation 406, may be based on the instantaneous grip configuration of the user's hand 402 on the UID 14.

At operation 602, as a precursor to determining the virtual center of rotation 404, the surgical robotic system 1 can determine a grip configuration of the user's hand 402 on the UID 14. The determination can include determining how the user is holding the UID 14 based on the proximity data. Such determination may include detecting, by one or more of the proximity sensors 316, positions of one or more fingers of the user's hand 402 on the UID 14. For example, the proximity sensors 316 can detect the contact points 403 between the fingers and the outer surface of the device body 304. The contact points 403 can be determined based on TOF data from TOF sensors mounted on the device head 312, or based on capacitive sensor data from capacitive sensors mounted on the grip components 310. The contact points 403 can define the grip configuration by defining the locations on the outer surface of the UID 14 at which the user's hand grips the UID 14. Accordingly, determining the grip configuration may include determining a spatial coordinate of each contact point 403 of the user's grip.

Determining the grip configuration may include determining a relative position between the contact points 403 of the user's grip and a reference point. For example, the reference point may be a center of mass of the UID 14, a center of inertia of the UID 14, or the default center of rotation 406. In an embodiment, the determination includes determining whether the positions of the one or more fingers of the user's hand 402 are anterior to or posterior to the sensor center of rotation 406 of the tracking sensor 302. This may include, for example, comparing a media or average axial location of the contact points 403 to an axial location of the reference point, and determining whether the user is gripping the UID 14 in front of or behind the reference point based on the comparison. Other techniques of defining the grip configuration may be used, as described below, and the described techniques are provided by way of example and not limitation.

Figure 7:
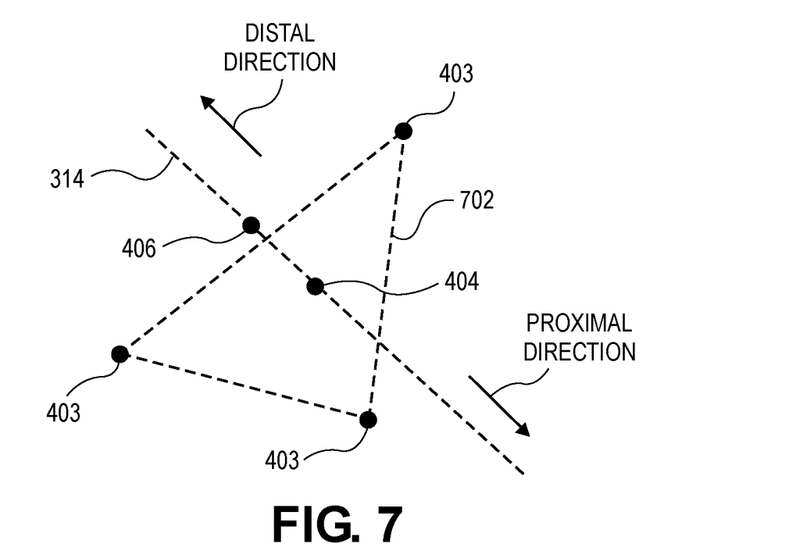
FIG. 7 is a schematic view of a grip configuration on a user interface device, in accordance with an embodiment.

Referring to FIG. 7, a schematic view of a grip configuration on a UID is shown in accordance with an embodiment. The grip configuration can be defined by the contact points 403. For example, the contact points 403 can define a plane 702, and an axial location of the plane 702 relative to the sensor center of rotation 406 may be used to determine the grip configuration. The user grip may include two contact points 403, corresponding to two fingers gripping the device body 304, and the plane 702 can be a plane 702 containing the contact points 403 and orthogonal to the central axis 314. Alternatively, the user's grip may include three or more contact points 403, corresponding to three or more fingers gripping the device body 304, and the plane 702 may be a plane 702 containing three of the contact points 403. These are examples, and other manners of determining the grip plane 702 as defined by the contact points 403 may be contemplated by one skilled in the art. In any case, once determined, the grip plane 702 may be compared to the sensor center of rotation 406 (or another reference point of the UID 14) to define the grip configuration. When the plane 702 is anterior to the sensor center of rotation 406, the grip configuration can be an anterior grip. When the plane 702 is posterior to the sensor center of rotation 406, the grip configuration can be a posterior grip. Of course, the plane 702 may intersect (or be within a predetermined distance of) the sensor center of rotation 406, in which case the grip configuration may be a medial grip.

At operation 604, the center of rotation 404 is determined based on the grip configuration. In any of the grip configurations describe above (the anterior grip, the medial grip, or the posterior grip), the center of rotation 404 can be estimated according to predetermined estimation rules. Estimation may not require extreme precision. For example, comparison of the grip plane 702 to the sensor center of rotation 406 may lead to the determination that the user is holding the UID 14 with the anterior grip. In response, the virtual center of rotation 404 may be set to a point on the central axis 314 midway between the sensor center of rotation 406 and the distal end 308 of the UID 14. Similarly, determination that the user is holding the UID 14 with the posterior grip may cause the virtual center of rotation 404 to be set to a point on the central axis 314 midway between the sensor center of rotation 406 and the proximal end 306 of the UID 14. The estimated virtual center of rotation 404 may not be exactly where the user expects the center of rotation 404 to be, but may be close enough to provide accurate and intuitive control of the surgical tool 7.

Still referring to FIG. 7, greater precision in the estimated virtual center of rotation 404 may be achieved using the contact points 403 as an input to determine the center of rotation 404. The user may intuitively expect the virtual center of rotation 404 to be radially between the contact points 403 of the fingers on the UID 14. Accordingly, the determination of the center of rotation 404 can include determining that the center of rotation 404 is at a location between the positions of the one or more fingers of the user's hand 402 on the UID 14. For example, the center of rotation 404 can be set to the location that is radially between the user's fingers, e.g., at a point within the UID 14.

In an embodiment, the virtual center of rotation 404 can be defined based on a geometric relationship between the grip plane 702 and another reference geometry of the UID 14. For example, the virtual center of rotation 404 can be determined to be a point along the central axis 314 at which the grip plane 702, as defined by the contact points 403, intersects the central axis 314.

In any case in which the user's grip is offset from a middle of the UID 14, the expected center of rotation may not coincide with the sensor center of rotation 406. The sensor center of rotation 406 can be the default center of rotation located at a datum of the coordinate system generated by the tracking sensor 302. Accordingly, the sensor center of rotation 406 can be fixed. That is, the sensor center of rotation 406 may be set during manufacturing or during calibration of the system, and once defined, may remain fixed throughout a surgical procedure. By contrast, the expected center of rotation can continuously or intermittently change during use of the UID 14. Thus, the expected center of rotation can be offset from the sensor center of rotation 406 by different distances throughout the surgery. Accordingly, the virtual center of rotation 404 can be set to a location offset from the default center of rotation 406 based on the user's grip.

In an embodiment, the determined center of rotation 404 is used to generate control commands to actuate a component of the surgical robotic system 1. For example, in the passive control embodiment of FIG. 6, the component can be the surgical tool 7 and movements of the surgical tool 7 can be mapped to input movements of the UID 14 about the virtual center of rotation 404. As described below with respect to the active control embodiment of FIG. 9, however, the component can be the UID 14 and haptic feedback provided by the UID 14 can be mapped to input loads applied to the surgical tool 7. In both embodiments, the mapping of the input to the output is adjusted based on how the user is holding the UID 14, e.g., with the anterior grip or the posterior grip.

Still referring to FIG. 6, at operation 606, in the passive control scenario, tracking data is received from the tracking sensor 302 of the UID 14. The tracking data is the input data used by the system to control how the end effector of the surgical tool 7 will respond. More particularly, the tracking data corresponds to movement of the tracking sensor 302 in six degrees of freedom, and represents the intended movement of the surgical tool 7 in six degrees of freedom.

At operation 608, the surgical robotic system 1 generates, based on the center of rotation 404 of the UID 14 and the tracking data from the tracking sensor 302, control commands to move the output component of the surgical robotic system 1. The component may be the surgical tool 7 of the surgical robotic system 1 such that generating the control commands is to actuate the surgical tool 7 based on the center of rotation 404 and the tracking data to move the surgical tool 7 in six degrees of freedom.

Figure 8:
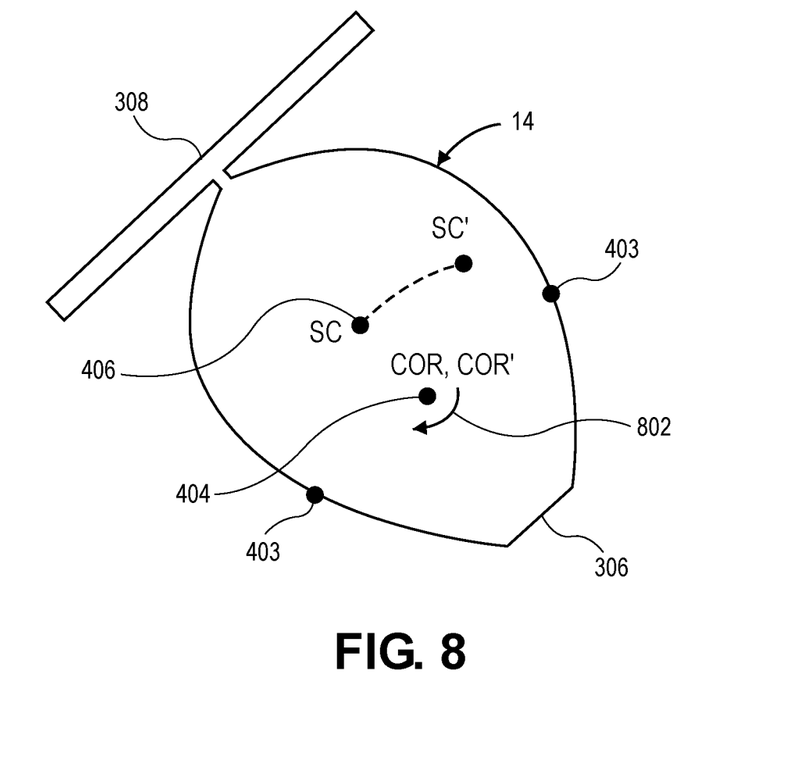
FIG. 8 is a schematic view of a movement of a user interface device about a center of rotation, in accordance with an embodiment.
Figure 9:
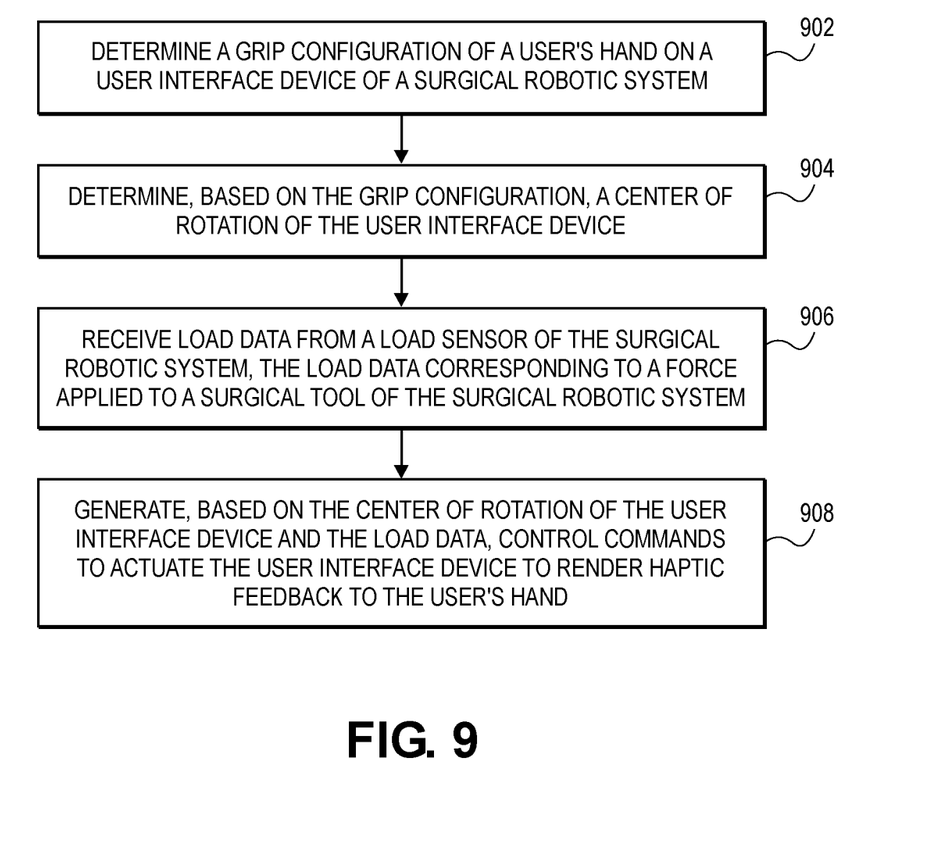
FIG. 9 is a flowchart of a method of actuating a user interface device of a surgical robotic system based on a center of rotation of the user interface device, in accordance with an embodiment.

Referring to FIG. 8, a schematic view of a movement of a UID about a center of rotation is shown in accordance with an embodiment. When the center of rotation 404 changes, e.g., based on the user changing the grip, the mapping between the input movements of the UID 14 and the output movements of the surgical tool 7 can be changed to cause the output movements to match the expectations of the user.

The expectations of the user depend on the user's grip. The user may be holding the UID 14 with the contact points 403 on the outer surface proximal to the sensor center of rotation 406. The user can impart an input movement 802 of pure rotation while holding the UID 14 near the proximal end 306. The user may therefore anticipate that the center or rotation of the surgical tool 7, e.g., a point along the cannula, will be controlled to also rotate with pure rotation. It will be appreciated, however, that pure rotation about the expected center of rotation 404, e.g., from orientation COR to COR', will instead cause a translation of the fixed center of rotation 404 from point SC to point SC'. In other words, if the center of rotation 404 used to control surgical tool movement is not adjusted, the point along the cannula will translate through space rather than experience pure rotation in space, as intended.

To avoid unintended movements of the surgical tool 7 and to cause the surgical tool movements to match the expectations of the user, the virtual center of rotation 404 can be adjusted from the fixed sensor center of rotation 406 to the center of rotation 404, and the input can be mapped to the output accordingly. More particularly, tracking data from the tracking sensor 302 can be mapped to movements about the virtual center of rotation 404 rather than about the sensor center of rotation 406. Thus, for example, when the tracking sensor 302 experiences translational movement from point SC to point SC', the system can map the movement to pure rotation of the surgical tool 7 about the tool center of rotation. Accordingly, the generated control commands cause movement of the surgical tool 7 that match the expectations of the user based on the user's handling of the UID 14.

Referring to FIG. 9, a flowchart of a method of actuating a UID of a surgical robotic system based on a center of rotation of the UID is shown in accordance with an embodiment. As noted above, the component of the surgical robotic system 1 for which control commands are generated can be the UID 14. For active controllers, such as haptic UIDs 14 with active torque degrees of freedom, changing the center of rotation 404 can be used in order to change the mapping to the surgical tool movement, as described above, and also to render different torques to the user holding the UID 14. More particularly, the UID 14 may be configured to render haptic feedback to the user based on input loads, e.g., reaction loads, applied to the surgical tool 7, and the behavior of the UID 14, e.g., the point at which the force is rendered to the user, can be adjusted to ensure that the user experiences a realistic emulation of the reaction load.

Operations 902 and 904 can be similar or identical to operations 602 and 604 described above. Accordingly, prior to remapping the input, such as a reaction load applied to the surgical tool 7 to a haptic feedback force generated at the UID 14, the surgical robotic system 1 can determine the center of rotation 404 of the UID 14 based on a grip configuration of the user's hand 402 on the UID 14.

At operation 906, the surgical robotic system 1 receives load data from a load sensor of the surgical robotic system 1. Referring again to FIG. 2, a load sensor 204 can be coupled to a joint of the robotic arm 4, or a portion of the surgical tool 7. The load sensor 204 can measure a reaction load or torque associated with a force 206 applied to the robotic arm 4 and/or surgical tool 7. For example, the load sensor 204 can generate load data corresponding to the force 206 applied to the surgical tool 7 when the surgical tool 7 is located within the patient 102. The force 206 can be a reaction force applied by the tissue of the patient 102 as the surgical tool 7 is moved within the patient 102. Accordingly, it will be appreciated that the force 206 may be applied at a location offset from the center of rotation of the surgical tool 7, and thus, would create a force and/or torque about the center of rotation of the surgical tool 7.

Referring again to FIG. 9, at operation 908, the surgical robotic system 1 generates control commands based on the center of rotation 404 of the UID 14 and the load data to actuate the UID 14 to render haptic feedback corresponding to the force 206. The control commands can render the haptic feedback, e.g., a haptic force or a haptic torque, to the user's hand 402 such that the user feels the reaction force 206 as if the user were holding the surgical tool 7 at the surgical site. The transformation of the reaction force 206 at the surgical tool 7 to the UID 14 can include mapping the reaction force 206 to the virtual center of rotation 404 rather than the sensor center of rotation 406. Using FIG. 8 as an example, if the reaction load is a reaction torque including pure rotation at the center of rotation of the surgical tool 7, haptic motors within the UID 14 can be actuated to cause a pure rotation about the virtual center of rotation 404 (accompanied by translational motion of the sensor center of rotation 406). Accordingly, the user can experience realistic haptic feedback corresponding to the loads seen by the surgical tool 7.

Figure 10:
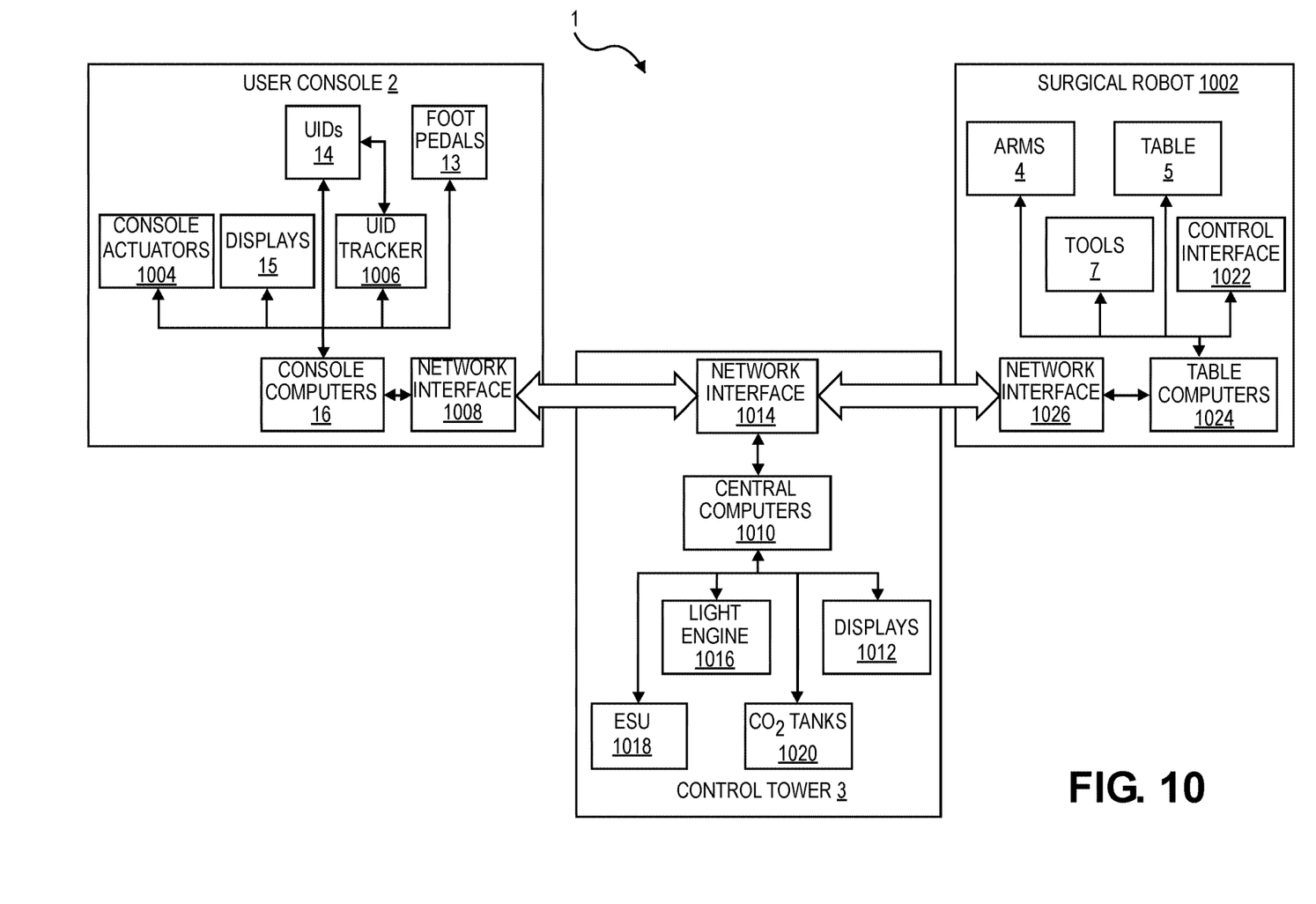
FIG. 10 is a block diagram of exemplary hardware components of a surgical robotic system, in accordance with an embodiment.

Referring to FIG. 10, a block diagram of exemplary hardware components of a surgical robotic system is shown in accordance with an embodiment. The exemplary surgical robotic system 1 may include the user console 2, a surgical robot 1002, and the control tower 3. The hardware components of the surgical robotic system 1 can include one or more processors configured to perform the methods described above. More particularly, the one or more processors, e.g., of the user console 2, may execute instructions stored on a non-transitory computer-readable medium to cause the surgical robotic system 1 to perform the methods described above. Furthermore, the surgical robotic system 1 may include other additional hardware components; thus, the diagram is provided by way of example and not limitation to the system architecture.

As described above, the user console 2 comprises console computer systems 16 and one or more UIDs 14. User console 2 can include console actuators 1004, displays 15, a UID tracker 1006, foot pedals 13, and a network interface 1008. A user or surgeon sitting at the user console 2 can perform robot-assisted surgeries by controlling the surgical robot 1002 using the one or more UIDs 14 and foot pedals 13. Positions and orientations of the UIDs 14 are continuously tracked by the UID tracker 1006, and status changes are recorded by the console computers 16 as user input and dispatched to the control tower 3 via the network interface 1008. The tracking data from the UID tracker 1006 and the proximity data from the UIDs 14 can be used by one or more processors of the console computers 16 to perform drop detection or grip-dependent control, as described above. Real-time surgical video of patient anatomy, instrumentation, and relevant software apps can be presented to the user on the high resolution 3-D displays 15 including open or immersive displays.

Unlike other existing surgical robotic systems, the user console 2 disclosed herein may be communicatively coupled to the control tower 3 over a single fiber optic cable. The control tower 3 can be a mobile point-of-care cart housing touchscreen displays, computers that control the surgeon's robotically-assisted manipulation of instruments, safety systems, graphical user interface (GUI), light source, and video and graphics computers. As shown in FIG. 10, the control tower 3 may comprise central computers 1010 including at least a visualization computer, a control computer, and an auxiliary computer, various displays 1012 including a team display and a nurse display, and a network interface 1014 coupling the control tower 3 to both the user console 2 and the surgical robot 1002. The control tower 3 may also house third-party devices, such as an advanced light engine 1016, an electrosurgical generator unit (ESU) 1018, and insufflator and $CO_2$ tanks 1020. The control tower 3 may offer additional features for user convenience, such as the nurse display touchscreen, soft power and E-hold buttons, user-facing USB for video and still images, and electronic caster control interface. The auxiliary computer may also run a real-time Linux, providing logging/monitoring and interacting with cloud-based web services.

The surgical robot 1002 comprises an articulated operating table 5 with a plurality of integrated arms 4 that can be positioned over the target patient anatomy. A suite of compatible tools 7 can be attached to or detached from the distal ends of the arms 4, enabling the surgeon to perform various surgical procedures. The surgical robot 1002 may also comprise control interface 1022 for manual control of the arms 4, table 5, and tools 7. The control interface can include items such as, but not limited to, remote controls, buttons, panels, and touchscreens. Other accessories such as trocars (sleeves, seal cartridge, and obturators) and drapes may also be needed to perform procedures with the system. In some variations the plurality of arms 4 include forearms mounted on both sides of the operating table 5, with two arms on each side. For certain surgical procedures, an arm mounted on one side of the table can be positioned on the other side of the table by stretching out and crossing over under the table and arms mounted on the other side, resulting in a total of three arms positioned on the same side of the table 5. The surgical robot 1002 can also comprise table computers 1024 and a network interface 1026, which can place the surgical robot 1002 in communication with the control tower 3.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A method of controlling a surgical robotic system based on a user's grip on a user interface device, the method comprising:
   determining a grip configuration of a user's hand on a user interface device of a surgical robotic system;
   determining, based on the grip configuration, a virtual center of rotation of the user interface device; and
   generating, based on the virtual center of rotation of the user interface device, control commands to actuate a component of the surgical robotic system.

2. The method of claim 1, wherein determining the grip configuration includes detecting, by one or more proximity sensors, positions of one or more fingers of the user's hand on the user interface device.

3. The method of claim 2, wherein the user interface device includes a tracking sensor having a sensor center of rotation, and wherein the virtual center of rotation does not coincide with the sensor center of rotation.

4. The method of claim 3, wherein determining the grip configuration includes determining whether the positions of the one or more fingers of the user's hand is anterior to or posterior to the sensor center of rotation of the tracking sensor.

5. The method of claim 2, wherein the virtual center of rotation is determined to be at a location between the positions of the one or more fingers of the user's hand on the user interface device.

6. The method of claim 2, wherein the one or more proximity sensors are time-of-flight sensors.

7. The method of claim 1 further comprising:
   receiving tracking data from a tracking sensor of the user interface device, wherein the tracking data corresponds to movement of the tracking sensor in six degrees of freedom; and
   wherein the component is a surgical tool of the surgical robotic system such that generating the control commands is to actuate the surgical tool based on the virtual center of rotation and the tracking data to move the surgical tool in six degrees of freedom.

8. The method of claim 1 further comprising:
   receiving load data from a load sensor of the surgical robotic system, wherein the load data corresponds to a force applied to a surgical tool of the surgical robotic system; and
   wherein the component is the user interface device such that generating the control commands is to actuate the user interface device based on the virtual center of rotation and the load data to render haptic feedback corresponding to the force to the user's hand.

9. A surgical robotic system, comprising:
   a surgical tool mounted on a surgical robotic arm;
   a user interface device; and
   one or more processors configured to:
      determine a grip configuration of a user's hand on the user interface device,
      determine, based on the grip configuration, a virtual center of rotation of the user interface device, and
      generate, based on the virtual center of rotation of the user interface device, control commands to actuate one or more of the surgical tool or the user interface device.

10. The surgical robotic system of claim 9, wherein determining the grip configuration includes detecting, by one or more proximity sensors, positions of one or more fingers of the user's hand on the user interface device.

11. The surgical robotic system of claim 10, wherein the user interface device includes a tracking sensor having a sensor center of rotation, and wherein the virtual center of rotation does not coincide with the sensor center of rotation.

12. The surgical robotic system of claim 10, wherein the virtual center of rotation is determined to be at a location between the positions of the one or more fingers of the user's hand on the user interface device.

13. The surgical robotic system of claim 9 further comprising:
   receiving tracking data from a tracking sensor of the user interface device, wherein the tracking data corresponds to movement of the tracking sensor in six degrees of freedom; and
   wherein generating the control commands is to actuate the surgical tool based on the virtual center of rotation and the tracking data to move the surgical tool in six degrees of freedom.

14. The surgical robotic system of claim 9 further comprising:
   receiving load data from a load sensor of the surgical robotic system, wherein the load data corresponds to a force applied to the surgical tool of the surgical robotic system; and
   wherein generating the control commands is to actuate the user interface device based on the virtual center of rotation and the load data to render haptic feedback corresponding to the force to the user's hand.

15. A non-transitory computer-readable medium storing instructions, which when executed by one or more processors of a surgical robotic system, cause the surgical robotic system to perform a method comprising:
   detecting, by one or more proximity sensors, positions of one or more fingers of a user's hand on a user interface device;
   determining, based on the positions of the one or more fingers, a virtual center of rotation of the user interface device; and
   generating, based on the virtual center of rotation of the user interface device, control commands to actuate a component of the surgical robotic system.

16. The non-transitory computer-readable medium of claim 15, wherein the user interface device includes a tracking sensor having a sensor center of rotation, and wherein the virtual center of rotation does not coincide with the sensor center of rotation.

17. The non-transitory computer-readable medium of claim 15, wherein the virtual center of rotation is determined to be at a location between the positions of the one or more fingers of the user's hand on the user interface device.

18. The non-transitory computer-readable medium of claim 15 storing instructions to cause the surgical robotic system to perform the method further comprising:

receiving tracking data from a tracking sensor of the user interface device, wherein the tracking data corresponds to movement of the tracking sensor in six degrees of freedom; and wherein the component is a surgical tool of the surgical robotic system such that generating the control commands is to actuate the surgical tool based on the virtual center of rotation and the tracking data to move the surgical tool in six degrees of freedom.

19. The non-transitory computer-readable medium of claim 15 storing instructions to cause the surgical robotic system to perform the method further comprising:

receiving load data from a load sensor of the surgical robotic system, wherein the load data corresponds to a force applied to a surgical tool of the surgical robotic system; and wherein the component is the user interface device such that generating the control commands is to actuate the user interface device based on the virtual center of rotation and the load data to render haptic feedback corresponding to the force to the user's hand.

20. The non-transitory computer-readable medium of claim 15, wherein the one or more proximity sensors are time-of-flight sensors.

* * * * *